(12) United States Patent
Molla et al.

(10) Patent No.: US 10,895,544 B2
(45) Date of Patent: Jan. 19, 2021

(54) MEASUREMENT OF LIQUID PARAMETERS USING A MICROFLUIDIC DEVICE

(71) Applicant: Schlumberger Technology Corporation, Sugar Land, TX (US)

(72) Inventors: Shahnawaz Hossain Molla, Watertown, MA (US); Farshid Mostowfi, Lexington, MA (US); John Ratulowski, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/503,569

(22) PCT Filed: Jun. 22, 2015

(86) PCT No.: PCT/US2015/036903
§ 371 (c)(1),
(2) Date: Feb. 13, 2017

(87) PCT Pub. No.: WO2016/028378
PCT Pub. Date: Feb. 25, 2016

(65) Prior Publication Data
US 2017/0227479 A1 Aug. 10, 2017

Related U.S. Application Data

(60) Provisional application No. 62/040,130, filed on Aug. 21, 2014.

(51) Int. Cl.
*G01N 33/28* (2006.01)
*G01N 25/02* (2006.01)
(Continued)

(52) U.S. Cl.
CPC ............... *G01N 25/02* (2013.01); *B81B 1/00* (2013.01); *G01N 21/03* (2013.01); *G01N 21/05* (2013.01);
(Continued)

(58) Field of Classification Search
CPC ........ G01N 15/08; G01N 25/02; G01N 25/66; G01N 33/2823; B81B 1/00; B81B 2201/058; B81B 2203/0338
See application file for complete search history.

(56) References Cited

U.S. PATENT DOCUMENTS 6,572,830 B1 * 6/2003 Burdon ................. F04B 19/006
156/89.11
6,599,436 B1 * 7/2003 Matzke ................ B01J 19/0093
216/2
(Continued)

FOREIGN PATENT DOCUMENTS

| EP | 542582 A1 | 5/1993 |
|---|---|---|
| EP | 1677100 B1 | 7/2006 |
| WO | 02/01211 A1 | 1/2002 |

OTHER PUBLICATIONS

International Search Report and Written Opinion issued in the related PCT application PCT/US2015/036903 dated Oct. 7, 2015 (11 pages).

(Continued)

*Primary Examiner* — Nathaniel T Woodward
*Assistant Examiner* — Philip L Cotey
(74) *Attorney, Agent, or Firm* — Cameron R. Sneddon

(57) ABSTRACT

A microfluidic apparatus has a microchannel that includes at least one vertically oriented segment with a top section having a relatively wide opening and a bottom section having a relatively narrow opening. The top section is larger in volume relative to the bottom sections, and the middle sections taper down in at least one dimension from the top (Continued)

section to the bottom section. One or tens or hundreds of vertically-oriented segments may be provided, and they are fluidly coupled to each other. Each segment acts as a pressure-volume-temperature (PVT) cell, and the microchannel apparatus may be used to determine a parameter of a fluid containing hydrocarbons such as the dew point of the fluid or the liquid drop-out as a function of pressure.

19 Claims, 8 Drawing Sheets

(51) Int. Cl.
G01N 21/25 (2006.01)
G01N 21/05 (2006.01)
G01N 21/03 (2006.01)
B81B 1/00 (2006.01)
G01N 25/66 (2006.01)

(52) U.S. Cl.
CPC .......... *G01N 21/25* (2013.01); *G01N 21/253* (2013.01); *G01N 25/66* (2013.01); *G01N 33/2823* (2013.01); *B81B 2201/058* (2013.01); *B81B 2203/0338* (2013.01); *G01N 2021/0346* (2013.01); *G01N 2021/0378* (2013.01); *G01N 2021/0382* (2013.01)

(56) References Cited

U.S. PATENT DOCUMENTS

| | | | | |
|---|---|---|---|---|
| 6,686,184 B1* | 2/2004 | Anderson | ............ | B01L 3/0258 435/174 |
| 7,074,690 B1 | 7/2006 | Gauri et al. | | |
| 7,134,486 B2* | 11/2006 | Santiago | ............ | B01D 19/0031 165/104.28 |
| 7,998,696 B2* | 8/2011 | Zaugg | ................. | G01N 33/491 422/412 |
| 8,340,913 B2* | 12/2012 | Mostowfi | .......... | G01N 15/1484 702/12 |
| 8,380,446 B2 | 2/2013 | Mostowfi et al. | | |
| 8,485,026 B2* | 7/2013 | Mostowfi | .......... | B01L 3/502784 73/152.23 |
| 9,073,018 B2* | 7/2015 | Ishiyama | ............. | B01F 5/0256 |
| 9,146,246 B2* | 9/2015 | Battrell | ............ | B01L 3/502738 |
| 2002/0023684 A1* | 2/2002 | Chow | ................. | B01J 19/0093 137/833 |
| 2003/0156992 A1* | 8/2003 | Anderson | ............ | B01D 61/18 422/502 |
| 2005/0266582 A1* | 12/2005 | Modlin | ................. | B01L 3/5027 436/164 |
| 2007/0048192 A1* | 3/2007 | Kartalov | ........... | B01L 3/502707 422/400 |
| 2008/0014589 A1* | 1/2008 | Link | .................... | C12Q 1/6806 435/287.2 |
| 2009/0095057 A1* | 4/2009 | Staats | ................ | G01N 30/7266 73/64.56 |
| 2009/0148869 A1* | 6/2009 | Zaugg | .................. | G01N 33/491 435/7.24 |
| 2009/0326827 A1* | 12/2009 | Mostowfi | .......... | B01L 3/502784 702/12 |
| 2010/0017135 A1 | 1/2010 | Mostowfi | | |
| 2010/0196212 A1* | 8/2010 | Reed | .................... | G01N 35/028 422/504 |
| 2010/0311085 A1* | 12/2010 | Zaugg | .................. | G01N 33/491 435/7.24 |
| 2011/0030466 A1* | 2/2011 | Mostowfi | .......... | B01L 3/502784 73/152.12 |
| 2011/0253222 A1* | 10/2011 | Arai | ...................... | B01F 5/0646 137/1 |
| 2011/0307186 A1 | 12/2011 | Mostowfi et al. | | |
| 2012/0031176 A1* | 2/2012 | Naessens | ............... | B01L 3/5027 73/61.59 |
| 2013/0100453 A1 | 4/2013 | Harrison et al. | | |
| 2013/0114369 A1* | 5/2013 | Ishiyama | ................. | B81B 1/00 366/149 |
| 2013/0295602 A1* | 11/2013 | Fowler | ................ | C12Q 1/6844 435/34 |
| 2013/0302883 A1* | 11/2013 | Fowler | .................... | C12P 19/34 435/287.2 |
| 2015/0065396 A1* | 3/2015 | Kiani | ................ | B01L 3/502784 506/26 |
| 2015/0114093 A1* | 4/2015 | Appleyard | ......... | G01N 15/1404 73/61.59 |

OTHER PUBLICATIONS

Concus, P. & R. Finn (1969) On the Behavior of a Capillary Surface in a Wedge. Proceedings of the National Academy of Sciences, 63, 292-299.
De Gennes, P. G. (1985) Wetting: Statics and dynamics. Reviews of Modern Physics, 57, 827-863.
Sharma, A. & R. Khanna (1999) Pattern formation in unstable thin liquid films under the influence of antagonistic short- and long-range forces. The Journal of Chemical Physics, 110, 4929-4936.
Wilinski, S. A., A. De Freitas & A. L. López de Ramos (2011) Visualization of liquid bridge rupture due to flow induced by corner effects. Chemical Engineering Science, 66, 3551-3556.
Bruno Pinho et al., A microfluidic approach for investigating multicomponent system thermodynamics at high pressures and temperatures, Royal Society of Chemistry 2014 (7 pages).
Taylor, B. (1712) Concerning the Ascent of Water Between Two Glass Plates. Philos. Trans. R. Soc. London, 538.
International Preliminary Report on Patentability issued in the related PCT application PCT/US2015/036903 dated Feb. 21, 2017 (9 pages).

\* cited by examiner 1844 psig 1769 psig 1741 psig 1688 psig 1551 psig 1486 psig

MEASUREMENT OF LIQUID PARAMETERS USING A MICROFLUIDIC DEVICE

CROSS-REFERENCE TO RELATED APPLICATION

The present application claims priority from U.S. Provisional Patent Application 62/040,130, filed Aug. 21, 2014, which is incorporated herein by reference.

BACKGROUND

Field

The subject disclosure relates to the analysis of fluids containing hydrocarbons. More particularly, the subject disclosure relates to the measurement of parameters of small samples of hydrocarbon fluid.

Description of Related Art

Retrograde condensates are hydrocarbon fluids that exhibit a dewpoint (i.e., the formation of a liquid phase from a gas phase) during isothermal depressurization at a temperature of interest. The presence of a liquid phase depends on temperature and pressure conditions in the reservoir that allows for condensation of liquid from vapor.

Prior art FIG. 1 shows the phase diagram of a typical gas condensate. The fluid is in gaseous form at pressures above the solid curve, while it forms liquid condensate once the pressure drops below the solid curve. Point 1 represents the gaseous state of the system at a given temperature. As the pressure drops at constant temperature, the system crosses the dew point curve (solid curve) and a liquid phase forms. Point 2 in FIG. 1 depicts the two-phase state of the system.

It should be appreciated that the formation of a liquid phase in the pores of formation rock during production of a gas field may result in reduced liquid recovery. Condensate dropout near the wellbore can significantly reduce the productivity index of a well. In severe cases the well can prematurely die decreasing overall recovery under naturally flowing conditions. Therefore, it is desirable to measure the dew point as well as liquid drop-out of such hydrocarbon fluids at reservoir conditions and plan the production accordingly. Indeed, phase behavior studies of lean gas condensates are of growing importance in reservoir fluid analysis. Saturation pressure (plat) or the dew point of a gas condensate is an important thermo-physical property of such fluids.

A common technique for phase behavior measurements for gas condensates uses conventional pressure-volume-temperature (PVT) cells, where the fluid is injected into a pressure-balanced glass chamber. The dew point may be detected by observing formation of mist in the chamber, when pressure and temperature are closely monitored. This technique has been available for many decades. Recently, a mirror has been incorporated in the chamber to improve the accuracy (see, e.g., European Patent EP 1 677 100 B1). Another method for the measurement of phase behavior uses a temperature controlled surface with monitoring of the variation in heat flux from the surface. When liquid condensate is formed on the surface, the heat flux decreases. Yet another method detects formation of condensates using a microwave resonator and utilizes the fact that the resonant frequency of a pressurized chamber changes when a liquid condenses inside (see, PCT International Patent Application Publication WO 02/01211 A1).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Microfluidic devices and methods using such devices are provided for facilitating detection of small amounts of liquid drop-out from condensates. In some embodiments, microfluidic devices formed from silicon wafers fabricated to create a microchannel including at least one vertical segment, each having a wide top section, a tapering collection section, and a narrow bottom section for detection of small amounts of liquid drop-out, where the wide, tapering and narrow sections are defined to ensure that the volume of liquid in the narrow section is less than or equal to 1.0%, or less than or equal to 0.1%, or less than or equal to 0.01%, or less than or equal to 0.005%, or less than or equal to 0.001% of the total segment volume. In one embodiment, the vertical segments are arranged in parallel with parallel inlets and parallel outlets. In another embodiment, the vertical segments are arranged in series. In one embodiment, the at least one vertical segment comprises ten or more vertical segments. In another embodiment, the at least one vertical segment comprises one hundred or more vertical segments. For purposes of this specification and the claims, the term "vertical" is to be understood as being oriented in a direction substantially aligned with gravitational forces.

In one embodiment, the microfluidic device is used to detect liquid drop-out by injecting a gas condensate into the microchannel of the device which is held in a vertical orientation. The pressure at the inlet and outlet of the microchannel are maintained above the dew point pressure. Once the microchannel is filled with a representative fluid sample, the pressure in the channel is hydrostatically reduced at both the inlet and outlet. As the local pressure in the gas drops below the dew point of the sample, a liquid phase is formed in the gas, and the emerging liquid creates a thin film on the microchannel surface. Since the channel is kept vertical, the liquid film drains under gravity, and surface forces arising from the interaction of liquid and gas with the surfaces with which they are in contact, towards the bottom of the microchannel where the liquid accumulates to form small droplets (e.g., 10-50 microns). The volume of these small droplets is a direct measure of the liquid drop-out from the volume of gas in the channel.

In one embodiment the dew point of a sample can be detected after a liquid is detected in the microchannel by increasing the pressure on the microchannel in, e.g., small steps until the droplets disappear back into the gas phase.

In one embodiment, the pressure can be reduced below the dew point to measure liquid drop-out at different pressures.

In one embodiment, using a microchannel with at least one segment having wide, tapering, and narrow portions as described, a liquid volume that is as small as 0.005% by volume of the fluid can be detected.

In one aspect, a microfluidic device utilizing a microchannel significantly increases the accumulation of liquid from the film drainage and allows for collection and detection of very small volumes of liquids in the channel.

Additional aspects, embodiments, objects and advantages of the disclosed methods may be understood with reference to the following detailed description taken in conjunction with the provided drawings.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show details in more detail than is necessary, the description taken with the drawings making apparent to those skilled in the art how the several forms of the subject disclosure may be embodied in practice. Furthermore, like reference numbers and designations in the various drawings indicate like elements.

As previously mentioned, the conventional PVT cell is the industry standard when making phase volume measurements. In a conventional PVT cell, when the pressure is dropped below the dew point pressure the amount of condensate liquid is measured by detecting the meniscus height and measuring the volume of liquid with respect to the total volume of sample in the cell ($V_{liq}/V_{total}$). The minimum detectable amount of liquid depends on the PVT cell design, e.g., cell volume, piston geometry etc.

Conventional methods using PVT cells encounter major difficulties when measuring the dew point of fluids with small liquid volume content (e.g., lean condensate). Dead volumes in conventional PVT cells limit the minimum measurable liquid volumes. While the cell volume can be increased in order to increase the amount of liquid collected at and below dew point pressure, the increase in accuracy that arises from a larger cell volume comes at the cost of significantly larger sample volume and operational difficulty.

Rather than increasing the cell volume, according to one aspect, a device for measuring dew points of fluids and for measuring drop-out volume utilizes a microfluidic device having a cell volume significantly smaller than conventional PVT cells (e.g., on the order of a milliliter or less versus tens or hundreds of milliliters). As will be described in more detail hereinafter, the microfluidic device includes a microchannel having at least one segment, which in some embodiments may comprise tens or hundreds of segments. In some embodiments, these microchannel segments resemble capillaries with small internal diameters. Due to the small dimensions of microchannels, the sample volume required in microfluidic systems amounts to a milliliter or less and often to only a few microliters. In microchannels/capillaries, the surface area in contact with the fluid is quite large compared to the volume of the fluid. As a result, the heat transfer between the sample and its surroundings is rapid and the temperature of the fluid in the microchannel can be changed rapidly.

Figure 1:
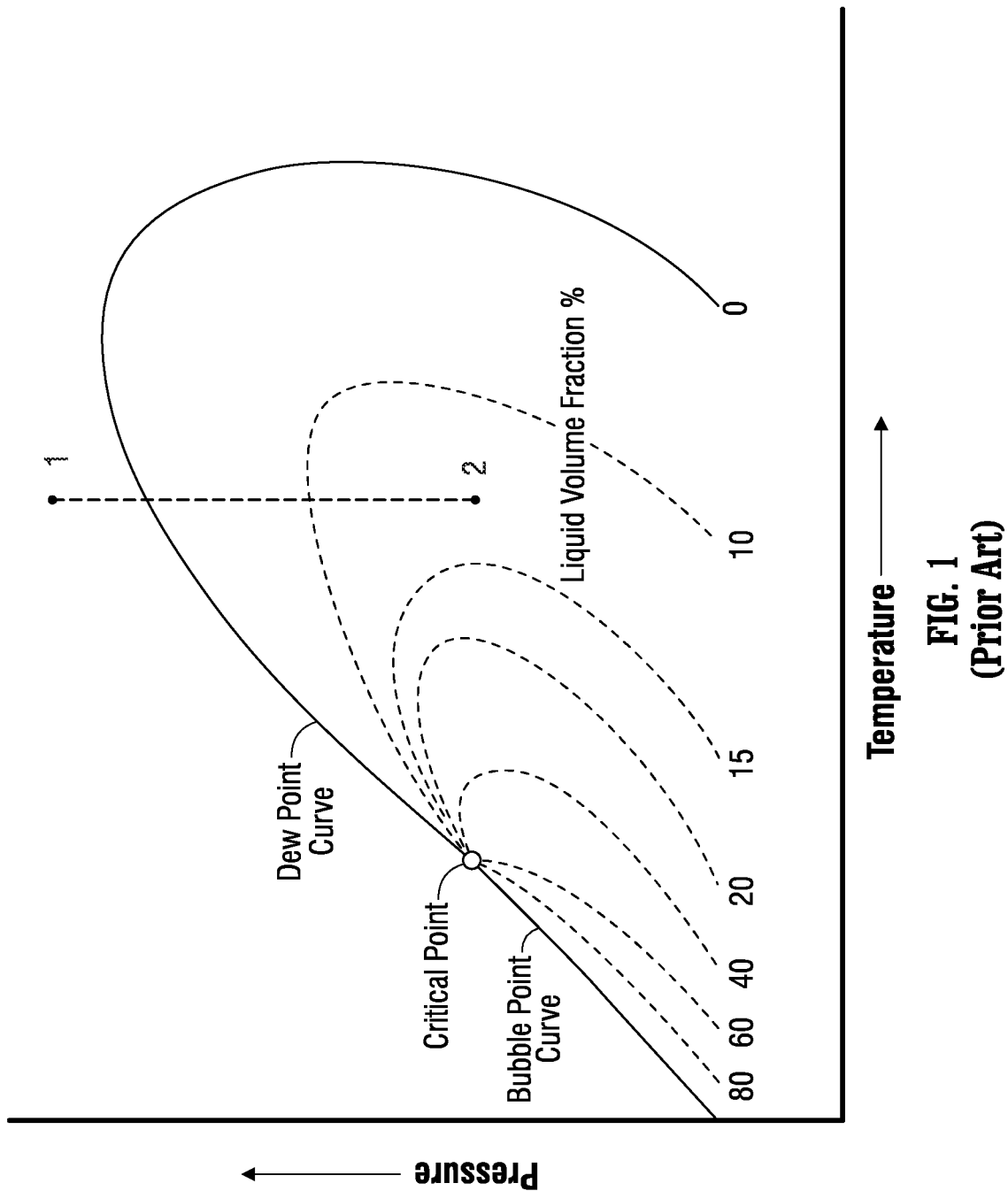
FIG. 1 is a prior art phase diagram for a gas condensate.
Figure 2A:
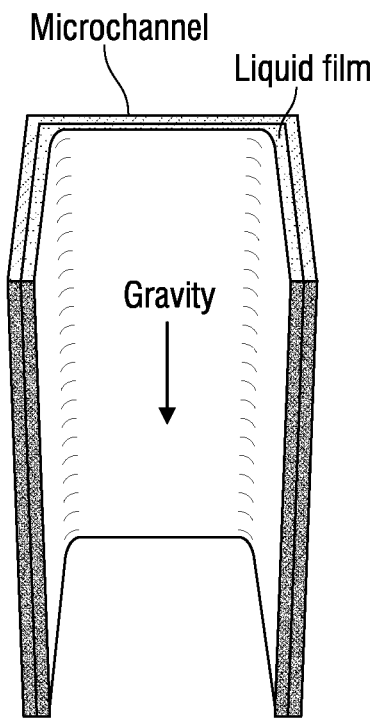
FIG. 2A is a schematic of a microchannel with a liquid film on a surface thereof.
Figure 2B:
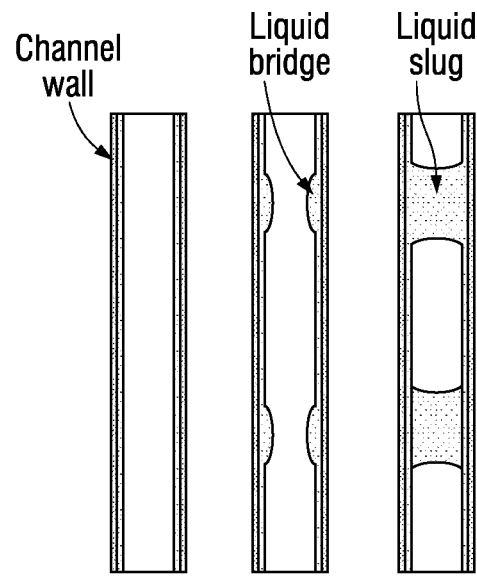
FIG. 2B is a schematic of the formation of a liquid slug in a microchannel.

On the other hand, the large surface-to-volume ratio can be an issue when testing gas condensate type fluids. Typically most hydrocarbon liquids exhibit strong affinity to the surface of the channel. As a result, the liquid wets the surface and forms a thin, stable liquid film, as shown in FIG. 2A. If the channel is straight, with uniform cross-section (i.e., no geometric variation) and oriented vertically, the film drains downward due to gravity and accumulates at the bottom of the channel. However, a residual thin film can contain/entrain a considerable amount of liquid even after gravity-driven drainage. The measurement of the film thickness, which is essential to estimate the liquid volume, is not straightforward. As the pressure is further decreased, the liquid film grows and at a certain point the film becomes unstable and forms liquid bridges across the channel. This process is schematically shown in FIG. 2B. The liquid bridges pull the liquid from the surrounding film and form slugs. When the liquid slugs are sufficiently large to be optically detected, the liquid volume can be accurately measured by measuring the length of the slugs. Until sufficient volume of liquid is available to form slugs, the liquid drop-out from the gas is typically not measurable. Smaller channel dimensions promote the formation of liquid slugs. However, since the liquid drop-out is proportional to the volume of gas available, simply making the channel dimensions smaller does not necessarily resolve the issue.

Figure 3:
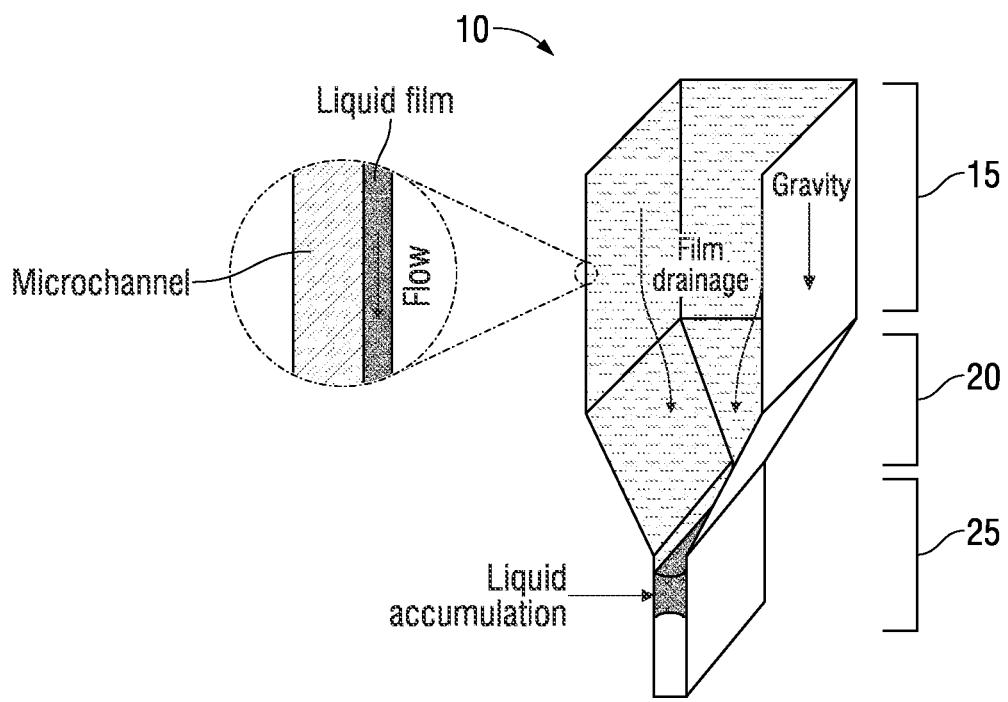
FIG. 3 is a schematic of a microchannel segment according to one embodiment.

As seen in the schematic of FIG. 3, according to one embodiment, a microchannel 10 is provided that increases the gravity-assisted flow of liquid from the film by incorporating capillary action. Such capillary action includes forces originating from the interaction of a gas-liquid interface with surfaces with which it comes in contact. Capillary forces at curved gas-liquid interfaces tend to force liquid from bulk to narrow capillaries. The goal is to direct the flow of liquid of the film from a large channel into a narrow channel where the small liquid volume in the film is sufficient to form slugs. To achieve this effect the vertical microchannel 10 is designed to have a top section 15 with a relatively large cross-sectional area, connected by a funnel 20 to a bottom section 25 having a relatively significantly smaller cross-section. The funnel 20 may assume a conical or other geometry which gradually reduces the cross-sectional area from the larger top section 15 to the smaller bottom section 25. The provided geometry acts as a collector and facilitates the accumulation of liquid from the top section 15.

More particularly, the relatively wide top section 15 of microchannel 10 is designed to act as a reservoir and hold a known volume of gas. When the pressure in the gas drops below dew point, the condensing liquid drains down the walls of the top section 15 and into the funnel 20 and collects at the bottom of the funnel 20. From there, the liquid flows or is drawn into the narrow bottom section 25 due to capillary action. Due to the small cross-section of the bottom section 25, the liquid entering the bottom section 25 forms liquid slugs which can be easily detected. In one aspect, the funnel angle can play a role in optimizing the capillary action which pulls liquid into the narrow bottom section 25 and may range from about 1 degree to about 179 degrees.

In one embodiment, the dimensions (width, depth, and length) of the top, conical, and bottom sections are defined so that the volume of liquid in the bottom section 25 is less than or equal to 1.0% of the total volume. In one embodiment, the dimensions are defined so that the volume of liquid in the bottom section 25 is less than or equal to 0.1% of the total volume. In one embodiment, the dimensions are defined so that the volume of liquid in the bottom section 25 is less than or equal to 0.01% of the total volume. In one embodiment, the dimensions are defined so that the volume of liquid in the bottom section 25 is less than or equal to 0.005% of the total volume. In one embodiment, the dimensions are defined so that the volume of liquid in the bottom section 25 is less than or equal to 0.001% of the total volume.

As the amount of liquid appearing from the gas phase increases with decreasing pressure, a gas-liquid meniscus forms in the bottom section 25, and can rise into the funnel 20 and eventually into the top section 15. The location (height) of the meniscus can be correlated to the volume fraction of liquid in the channel. The volume in the microchannel can be calculated based on the channel width, depth, and length of each section. This may be obtained by accurate measurement of channel dimensions using standard measurement techniques such as optical profilometer and scanning electron microscope (SEM) imaging.

In one embodiment, one or more microchannels are fabricated in a silicon wafer using techniques described in U.S. Pat. Nos. 8,485,026 and 8,340,913, both of which are hereby incorporated by reference herein in their entireties. The microchannel(s) is/are etched in silicon using conventional Deep Reactive Ion Etching (DRIE) and closed with a glass substrate. The permanent bonding between silicon and glass can be achieved by conventional anodic bonding. It should be noted that microchannels can also be fabricated in other materials such as glass, metal, sapphire, and ceramic.

Figure 4:
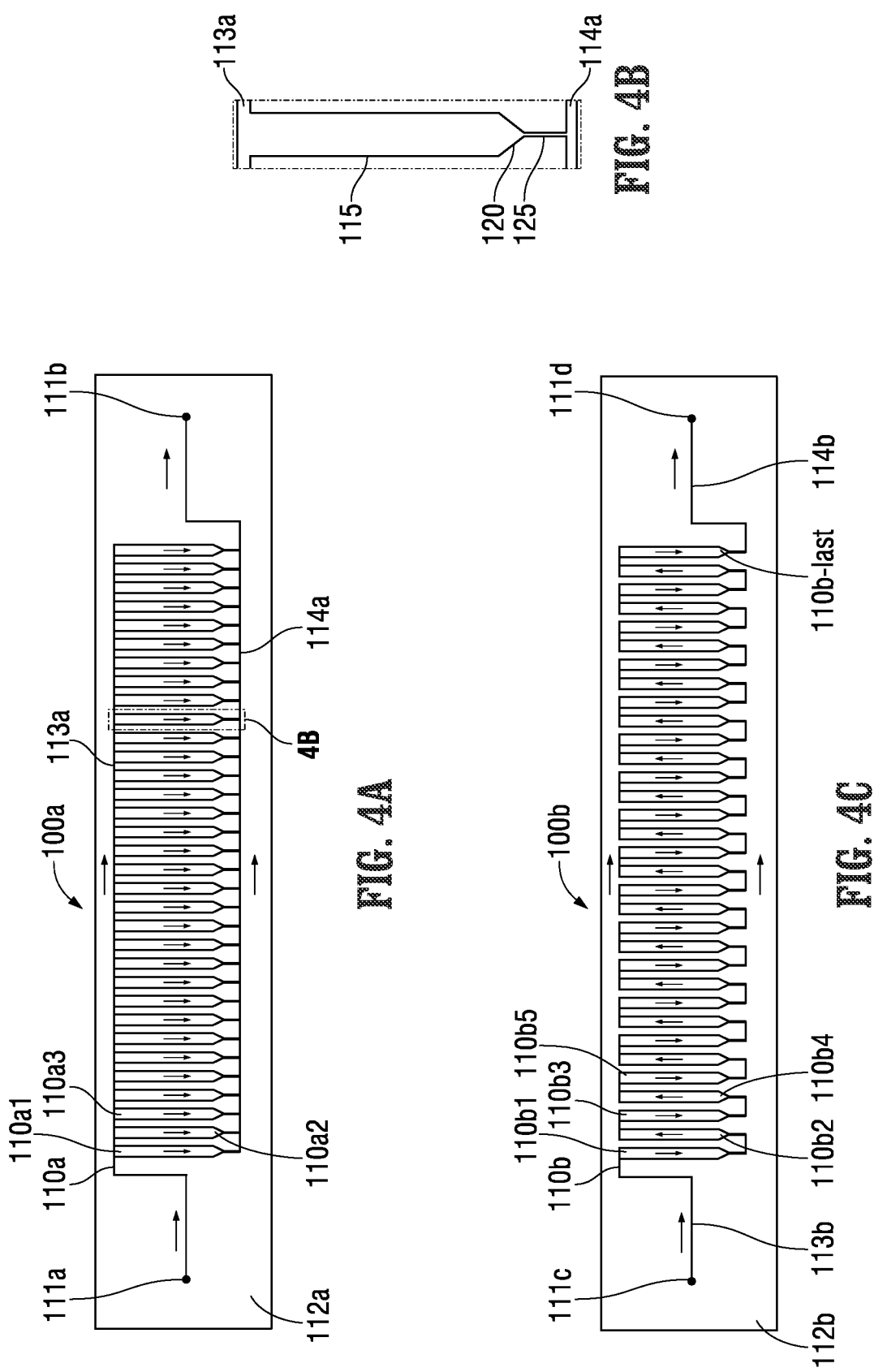
FIG. 4A is a schematic of a microchannel incorporating numerous segments of FIG. 3 in parallel.
FIG. 4B is a schematic of a segment of FIG. 4A coupled to inlet and outlet channels.
FIG. 4C is a schematic of a microchannel incorporating numerous segments of FIG. 3 in series.

One embodiment of a microfluidic device 100a incorporating a microchannel 110a is depicted in FIG. 4A. Two small holes 111a (inlet), 111b (outlet) are created in a silicon substrate 112a to supply fluids to the microchannel 110a. The microchannel 110a comprises one or more, e.g., one, ten, tens, a hundred, hundreds, or even a thousand or more, individual parallel vertical segments 110a1, 110a2, 110a3 . . . which are coupled to the inlet 111a and outlet 111b by lines 113a, 114a. Each segment may have three sections, namely a wide section (115 in FIG. 4B) coupled to line 113a, a tapered section 120, and a narrow section 125 coupled to line 114a. Thus, when fluid is supplied to the microfluidic device 100a, it flows from the inlet 111a, into inlet line 113a and in parallel through the vertical segments 110a1, 110a2, 110a3 . . . and outlet line 114a to the outlet 111b. Alternatively, fluid may be introduced through the outlet 111b. The total volume of sections 115, 120, and 125 makes up the volume of each segment. In the design shown, the dimensions (width, depth, and length) of the sections are defined to ensure that the volume of liquid in the section 125 is no more than 0.005% of the total segment volume to permit detection of small liquid drop-out. Sample dimensions are seen in Table 1:

TABLE 1

| Section | Width (microns) | Depth (microns) | Length (microns) |
| --- | --- | --- | --- |
| 115 | 250 | 100 | 6500 |
| 120 | 250-10 (tapering) | 100-10 (tapering) | 1500 |
| 125 | 10 | 10 | 100 |

In other embodiments, the dimensions can be modified to alter the minimum liquid detection. Thus, while the combined volume of sections 115 and 120 is considerably larger than the volume of the narrow detection section 125, the volume of section 125 may be less than or equal to 1.0% of the total segment volume, less than or equal to 0.1% of the total segment volume, less than or equal to 0.01% of the total segment volume, or less than or equal to 0.001% of the total segment volume.

Another embodiment of a microfluidic device 100b seen in FIG. 4C incorporates a microchannel 110b having a plurality of, e.g., ten or more, tens, a hundred or more, or hundreds, or even a thousand or more, individual vertical segments 110b1, 110b2, 110b3, 110b4, 110b5 . . . arranged in series, with each segment having a wide section 115, a tapered section 120, and a narrow section 125 as in FIG. 4B and of desired volumes as previously described with respect to FIGS. 4A and 4B. Two small holes 111c (inlet), 111d (outlet) are created in a silicon substrate 112b to supply fluids to the microchannel 110b, with a first of the vertical segments 110b1 coupled to inlet 111c by line 113b, and the last of the vertical segments 110b-last coupled to the outlet 111d by line 114b. However, rather than having the wide section of each vertical segment coupled to the inlet line 113b and each narrow section coupled to the outlet line 114b as in FIG. 4A, the narrow section of vertical segment 110b1 is coupled to the narrow section of vertical segment 110b2, the wide section of vertical segment 110b2 is coupled to the wide section of vertical segment 110b3, the narrow section of vertical segment 110b3 is coupled to the narrow section of vertical segment 110b4, the wide section of vertical segment 110b4 is connected to the wide section of vertical segment 110b5, and so on. Thus, when fluid is introduced into microfluidic device 100b, the fluid flows from the inlet 111c, and sequentially through the vertical segments 110b1, 110b2, 110b3, 110b4, 110b5 . . . , (sometimes from top down and sometimes from bottom up) to the outlet.

According to one aspect, other embodiments of a microfluidic device with multiple vertical segments may be provided such that sample is provided to multiple vertical segments. Regardless, by providing multiple vertical segments, each segment acts like an independent PVT cell. By arranging a plurality, e.g., tens or hundreds of individual segments on a single device, liquid drop-out of a sample is effectively measured in a plurality of independent PVT cells.

Figure 5:
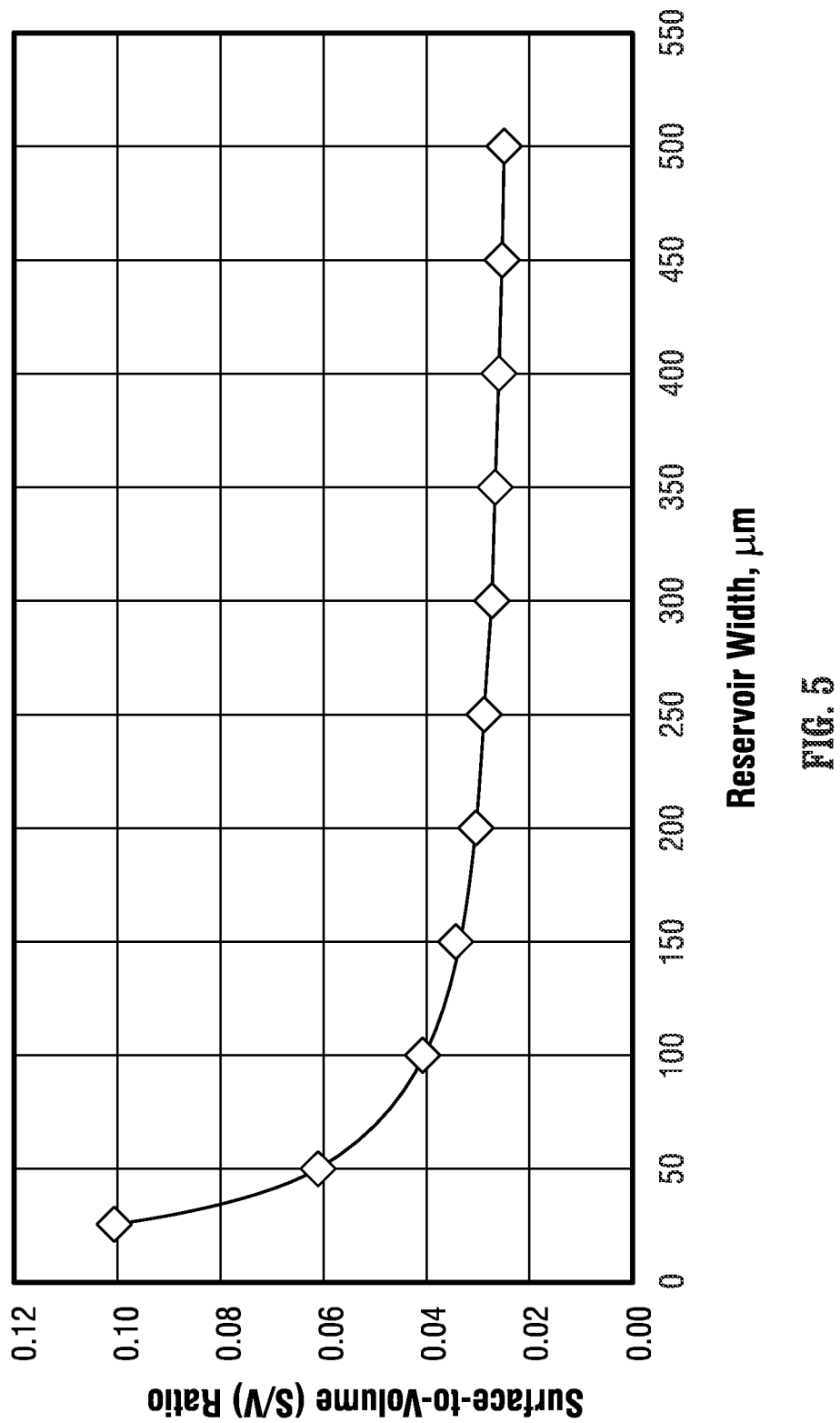
FIG. 5 is a graph plotting surface-to-volume ratio versus reservoir width.

In one aspect, the dimensions of the segments of the embodiments may be selected to minimize the surface-to-volume (SN) ratio of the microchannels. In one aspect, it may be important to reduce the surface area which is wetted by the liquid film. FIG. 5 shows an example of variation of surface-to-volume ratio with increasing width of the reservoir top section 115 of a microchannel segment.

Figure 6:
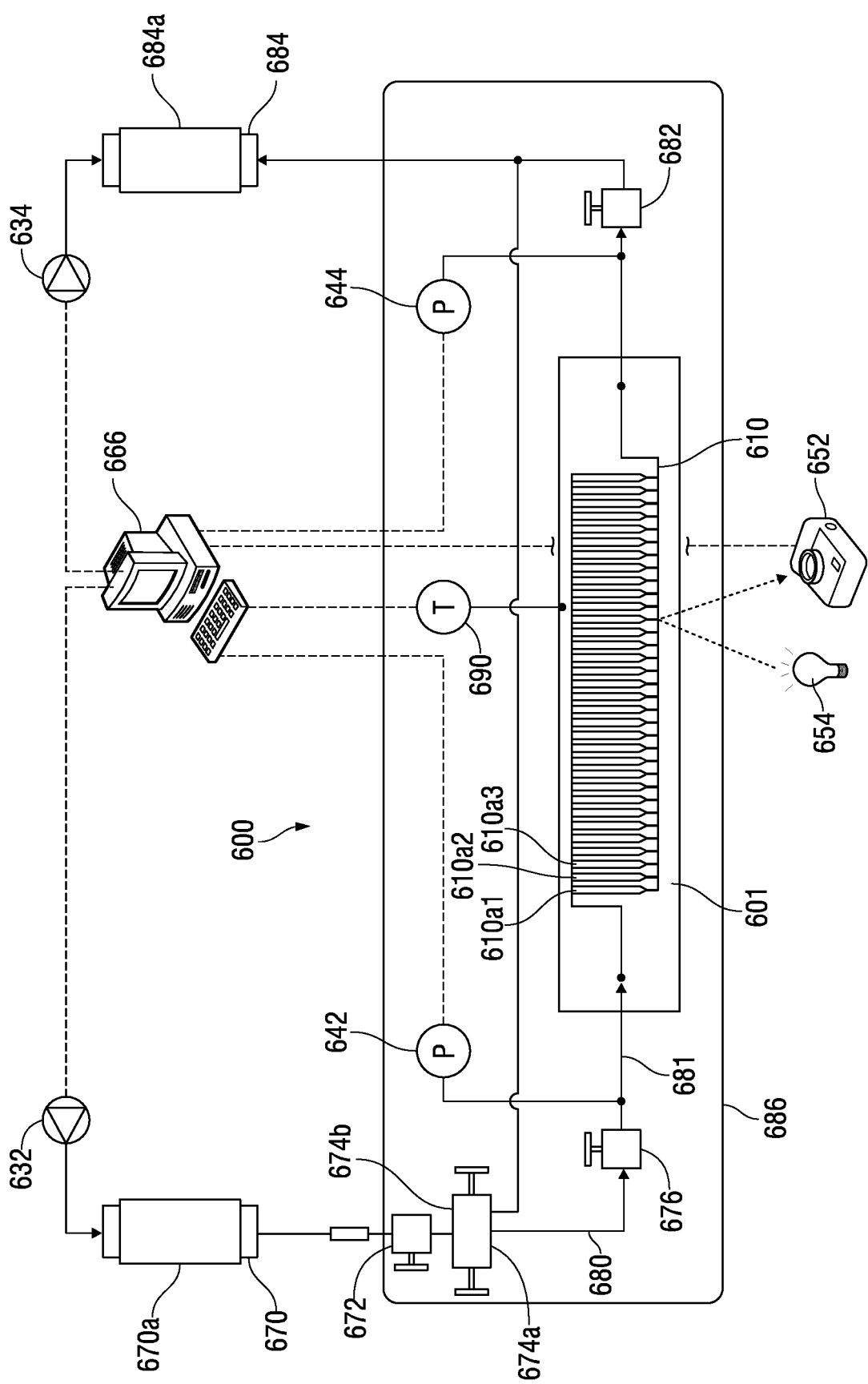
FIG. 6 is a schematic diagram of a system for determining dew point and liquid volume fraction of a fluid.
Figure 7A:
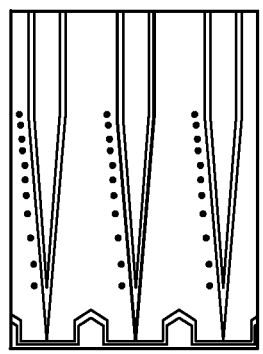
FIGS. 7A-7F are schematics of multiple segments of a microchannel showing liquid volume in the microchannel for a sample at different pressures.
Figure 7B:
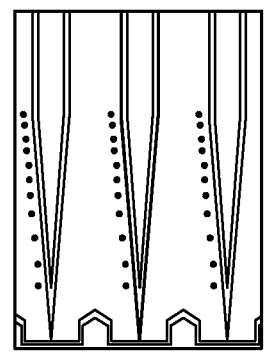
Figure 7C:
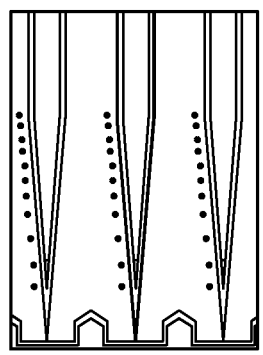
Figure 7D:
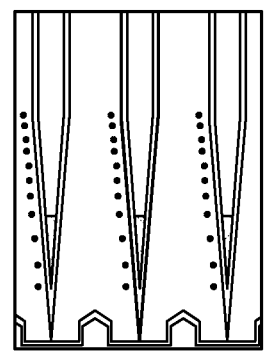
Figure 7E:
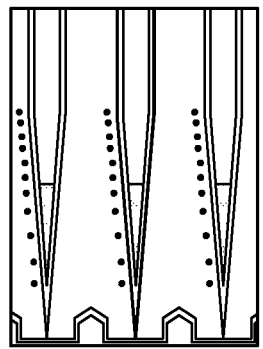
Figure 7F:
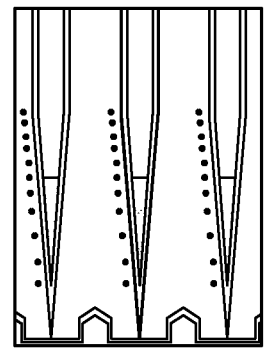

Turning now to FIG. 6, an apparatus 600 is provided for measuring the liquid volume fraction of a hydrocarbon fluid sample, and for measuring dew point of the sample. The apparatus 600 includes a microfluidic device 601 such as microfluidic device 100a having a microchannel 610 with multiple vertical segments 610a1, 610a2, 610a3 . . . , two high pressure syringe pumps 632, 634 (ISCO 65D, available from Teledyne ISCO of Lincoln, Nebr., USA), two pressure sensors 642, 644 (available from Sensotreme GmbH of Ramsen, Switzerland, accuracy ±10 psi (0.7 kg/square cm)), a charge-coupled device (CCD) camera 652 (PL-B782U, available from PixeLINK, Ottawa, Ontario, Canada), a light source 654, and a computer 666. The sample is held in a high pressure sample bottle 670, above its saturation pressure and is injected into the microfluidic device 601 through a set of valves 672, 674a, 676 and stainless steel tubing (1/16 inch (1.6 mm) internal diameter) 680, 681. The injection pressure is measured using a pressure gauge 642 just before the input port. The fluid is collected via valve 682 in another sample bottle 684 on the other side of the microfluidic device 601. To maintain a constant condition, the pressure of the exit sample bottle 684 is controlled using pressure sensor 644 and high pressure syringe pump 634 which may both be coupled to the computer 666. In addition, if desired, the valves such as valves 672, 674a, 674b, 676, 682, and the input pressure sensor 642 and pump 632 may all be coupled to and controlled by the computer 666.

In one embodiment, the sample is injected into the microchannel 610 at a pressure higher than its saturation point. The sample flows through valves 672, 674a, 676, and 682, while valve 674b is kept closed. The pressure in sample bottle 684 is initially kept the same as the inlet pressure, and then the pressure is slowly reduced until the microchannel 610 is filled with the test fluid. Pressure in the system is carefully monitored using pressure sensors 642 and 644 to ensure the sample remains in a single phase. With the microchannel 610 filled with the fluid, the system is isolated from sample bottle 670 by closing valve 672. Then valve 674b is opened and the pressure at both inlet and outlet is controlled by pump 634. The pressure in the microchannel 610 is slowly reduced to conduct a PVT test. The pressure drop results in a phase change of the fluid, leading to appearance of the liquid phase which is identified by the computer 666 based on signals received by camera 652 resulting from reflection and/or transmission of light from light source 654 due to the presence of liquid in the microfluidic device 601. The pressure at which the presence of a small amount of liquid is first detected in narrow section 125 or outlet line 114a in FIG. 4B is identified as the phase transition point (i.e., the dew point in case of liquid appearing in gas. In addition, once the presence of liquid is identified, the pressure in the microchannel 610 may be increased to find the point at which the liquid phase disappears (i.e., the dew point). Again, the camera 652 and computer 666 may be used to make this determination. Further, the camera 652 and computer 666 may be used in conjunction with the microchannel segments to identify the liquid drop-out volume (or volume drop-out fraction) at a given temperature and pressure. As previously indicated, the segments may be marked by height to represent different liquid percentages. Then, the camera 652 and computer 666 may be used to find the meniscus location relative to the markings. It should be noted that the meniscus location may also be detected by non-visual techniques, e.g. by using capacitive/impedance (electromagnetic), acoustic, or piezoelectric sensors embedded in the microchannels or outside the microchannels.

In one aspect, in conducting a PVT test, the pressure drop in the microchannel 610 is accomplished while many of the components of the system are kept at a constant (test) temperature, e.g., by placing them in a temperature-controlled enclosure 686. The temperature-controlled environment may include one or more optical access windows for the camera 652, light source 654, and other optical components, and a temperature sensor 690 may be provided and coupled to the computer 666, if desired. The access windows may be glass, sapphire, or other material which will not impact the ability of the camera to detect the presence of the liquid. The sample bottles 670, 684 may also be temperature-controlled using heating jackets 670a, 684a.

Two gas condensate samples were tested using the apparatus of FIG. 6 for validation. Sample 1 was a binary mixture of methane and n-butane, tested at 21.0° C. and 30.5° C. Sample 2 was a multicomponent mixture, tested at 60.0° C. Constant-composition-expansion (CCE) tests were conducted for each sample in a conventional PVT system for comparison purposes.

FIGS. 7A-7F show photographs of the tapering and bottom sections of three segments of the microchannel in a vertical orientation during a test with Sample 1. The dots on the left-hand side of each conical section serve as a visual guide of volume collected in each cone. The location of the dots was calibrated to represent 0.5 to 10% liquid volume fraction. When the pressure was dropped from 1844 psig (129.6 kg/square cm gauge) to 1769 psig (124.4 kg/square cm gauge), liquid slugs first appeared in the narrow channels connecting two vertical channels. The pressure was then slowly increased to detect the disappearance of the liquid phase, i.e., the dew point, which in this case was found to be 1788 psig (125.7 kg/square cm gauge). After the dew point was found, the pressure was further dropped, e.g., to 1741 psig (122.4 kg/square cm gauge), and thereafter to 1688 psig (118.7 kg/square cm gauge), 1551 psig (109.0 kg/square cm gauge), and 1486 psig (104.5 kg/square cm gauge), and as seen in FIGS. 7C, 7D, 7E, and 7F, liquid forming a curved meniscus at the gas-liquid interface appeared and started to move upward in the tapered sections of the segments. The meniscus location in the vertical direction was uniform in all the segments. At each pressure, the meniscus in the segments was monitored to detect any change in liquid height. This continuous monitoring showed that the condensation of the liquid reached equilibrium within ten to fifteen minutes. To establish the time required to reach equilibrium, the height of the meniscus was also monitored over a period of twelve hours. No significant change was measured after the initial fifteen minutes. At each pressure, the meniscus heights in multiple segments were measured and the average was used to calculate the liquid volume fraction. The pump flow rate was fixed to 50 microliters/minute during pressure changes between two steps.

Figure 8:
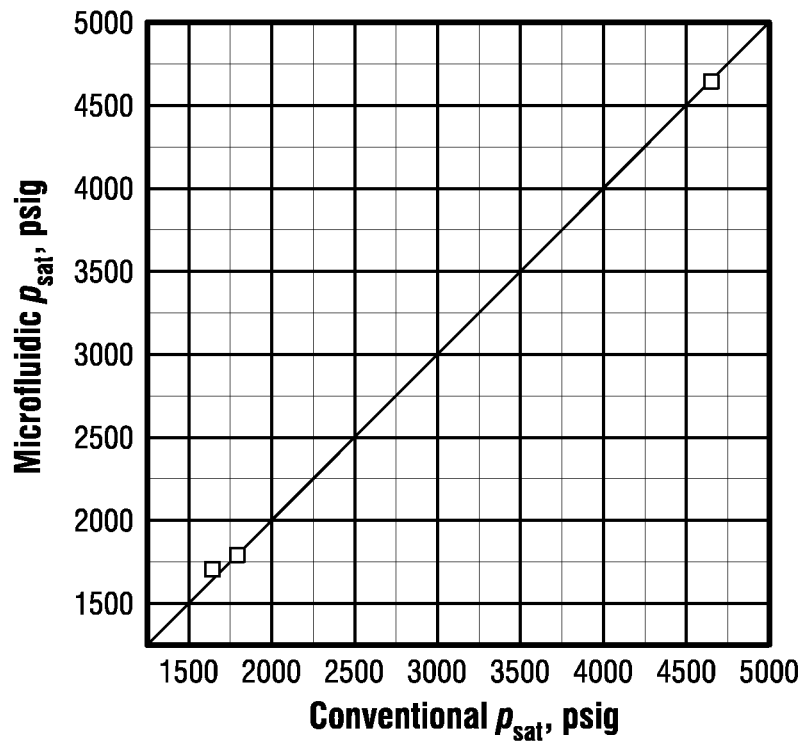
FIG. 8 is a graph plotting dew point measurements made using conventional techniques and using the system of FIG. 6.

FIG. 8 shows a comparison between the dew point measurements ($p_{sat}$) for the two samples, measured by the microfluidic apparatus of FIG. 6 and conventional PVT analysis. The measurements are in good agreement. The maximum difference between the measurements was less than 50 psig (3.5 kg/square cm gauge). The repeatability of the measurement technique was excellent. The standard deviation was 12 psig (0.8 kg/square cm gauge) based on triplicate runs for Sample 2.

Figure 9A:
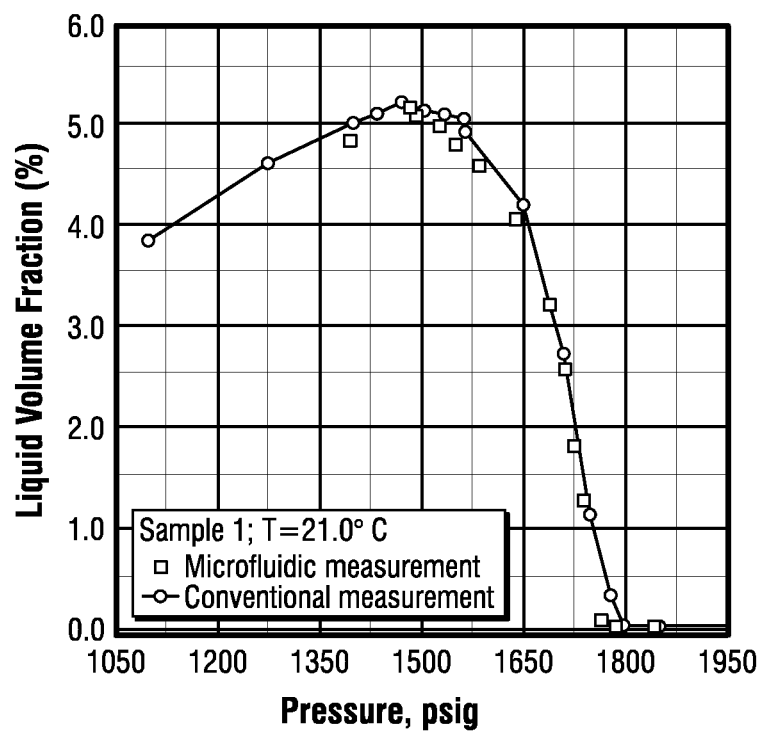
FIGS. 9A and 9B are graphs plotting liquid volume fraction of a sample as a function of pressure at two different temperatures using conventional techniques and using the system of FIG. 6.
Figure 9B:
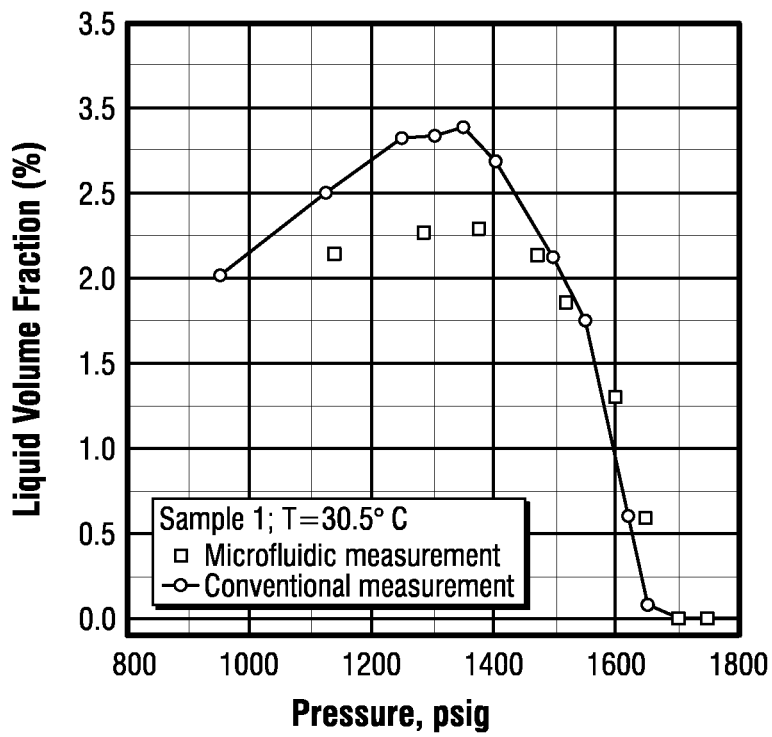
Figure 10:
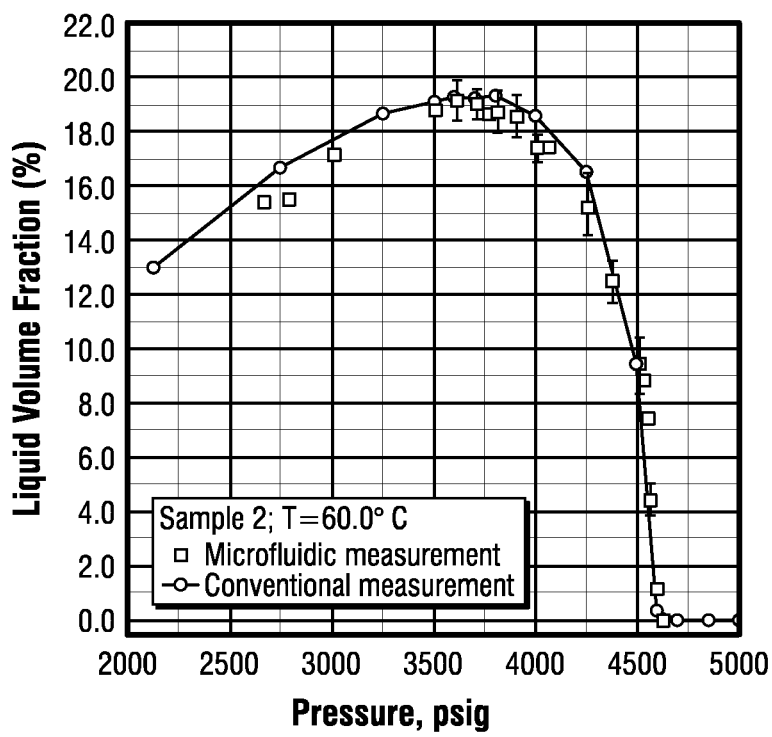
FIG. 10 is a graph plotting liquid volume fraction of another sample as a function of pressure at a given temperature using conventional techniques and using the system of FIG. 6.

The microfluidic measurements of liquid volume fraction are compared with conventional PVT analysis measurements in FIGS. 9A, 9B for Sample 1 and in FIG. 10 for Sample 2. In FIGS. 9A, 9B, and 10, the circles and line represent conventional laboratory measurement, whereas, the squares represent microfluidic measurements. FIG. 9A shows the liquid content percentage measured at different pressures for Sample 1 at 21.0° C., while FIG. 9B shows the liquid content percentage measured at different pressures for Sample 1 at 30.5° C. Liquid drop-out measured as a function of pressure using the microfluidic technique agrees well with the lab measurements throughout the entire pressure range, particularly at the lower temperature of 21.0° C. (FIG. 9A).

FIG. 10 compares the measurements made on Sample 2 at 60.0° C., and again shows good agreement between the determinations made using the microfluidic technique and using standard PVT equipment. In addition, FIG. 10 shows the repeatability of the liquid drop-out measurements by providing error bars showing the standard deviation from triplicate runs using the microfluidic apparatus. The expansion of the gas phase volume in the microchannel between two pressure steps was taken into account for the calculation of liquid volume fraction at each pressure step. In addition, the measurements plotted in FIGS. 9A, 9B, and 10 demonstrate that very small volumes of liquid drop-out (e.g., 0.5% at 1630 psig (114.6 kg/square cm gauge) in FIG. 9B) can be obtained with the microfluidic apparatus that does not require a large volume of sample.

In one aspect, some of the methods and processes described above, such as a dew point calculation and liquid drop-out volume fraction are performed at least partially by a "computer". The term "computer" should not be construed to limit the embodiments disclosed herein to any particular device type or system. The computer may include a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the computer or processor may include discrete electronic components coupled to a printed circuit board, integrated circuitry (e.g., Application Specific Integrated Circuits (ASIC)), and/or programmable logic devices (e.g., a Field Programmable Gate Array (FPGA)). Any of the methods and processes described above can be implemented using such logic devices.

According to one aspect, information measured by the system, such as the dew point, or such as the liquid drop-out of the fluid as a function of pressure may be plotted on a computer monitor or other screen, or on paper.

Based on all of the above, according to one aspect, a method of measuring a parameter of a small amount of fluid containing hydrocarbons, includes introducing a small amount of fluid into a microchannel having a volume on the order of a milliliter or less and including at least one vertically-oriented segment as previously described, modifying the pressure or temperature of the fluid in the microchannel, monitoring the microchannel to identify a change of state of fluid in the microchannel, and measuring a parameter of the fluid based on the change of state. For example, the dew point of the fluid may be measured by monitoring the change of state of the fluid as the pressure and/or temperature of the fluid is changed. Similarly, the liquid drop-out of the fluid as a function of pressure may be measured by monitoring the presence and build-up of liquid in the microchannel as the pressure is changed.

Although only a few examples have been described in detail above, those skilled in the art will readily appreciate that many modifications are possible in the examples without materially departing from this subject disclosure. Thus, by way of example only, and not by way of limitation, while various embodiments of microfluidic devices have been described with segments of particular geometries and arrangements, it will be appreciated that different microfluidic devices may be used, and they may be used in different arrangements, provided that the narrow section in which liquid gathers represents a very small percent of the total volume of the segment, and provided that the total volume of the segments is sufficient to test a sample. Also, while a particular test apparatus using a microfluidic device, pumps, pressure sensors, valves, a light source, camera, and computer was described, it will be appreciated that other arrangements using the microfluidic device could likewise be utilized. Thus, by way of example only, the valves may be manual or electronic, the pressure sensors may be coupled to the computer or may be viewed manually, etc. Further, it will be appreciated that while the dew point and liquid drop-out were measured by holding the temperature steady and by changing the pressure to the microfluidic device, in other embodiments the pressure may be held steady and the temperature varied in order to find the dew point, liquid drop-out, or other parameters of the fluid being investigated. Accordingly, all such modifications are intended to be included within the scope of this disclosure as defined in the following claims. In the claims, means-plus-function clauses are intended to cover the structures described herein as performing the recited function and not only structural equivalents, but also equivalent structures.

What is claimed is:

1. A microfluidic apparatus for measuring a parameter of a fluid containing hydrocarbons, comprising:
a microchannel including at least one vertically-oriented segment, each segment having:
a wide section having a first opening;
a non-tapered narrow section having a second opening; and
a tapered section between the wide and non-tapered narrow sections, the tapered section tapering down in at least one dimension from the wide section to the non-tapered narrow section, wherein the first opening is wider than the second opening, and the wide section is larger in volume relative to the non-tapered narrow section,
wherein the at least one segment comprises at least two segments arranged in series or wherein the at least one segment comprises at least two segments arranged in parallel with the wide sections of all of the segments coupled by a first fluid line, and the non-tapered narrow sections of all of the segments coupled by a second fluid line.

2. A microfluidic apparatus according to claim 1, wherein the microchannel is etched in silicon, glass, metal, sapphire, or ceramic and sealed closed by a cover, leaving an inlet and an outlet.

3. A microfluidic apparatus according to claim 1, wherein the at least one segment comprises at least ten segments.

4. A microfluidic apparatus according to claim 3, wherein the at least one segment comprises at least one hundred segments.

5. A microfluidic apparatus according to claim 1, wherein each non-tapered narrow section has at least one dimension of 10 microns.

6. A microfluidic apparatus according to claim 1, wherein each non-tapered narrow section is sized to draw fluid from a respective tapered section by capillary action.

7. A microfluidic apparatus according to claim 1, further comprising a temperature-controlled enclosure in which the microchannel is located.

8. A microfluidic apparatus according to claim 1, further comprising:
a light source arranged to illuminate at least the non-tapered narrow section of the at least one microchannel segment;
a light sensor arranged to sense light which is at least one of reflected from and transmitted through the non-tapered narrow section of the at least one microchannel segment; and
a computer coupled to the light sensor for identifying a parameter of fluid in the microchannel based on information received from the light sensor.

9. A microfluidic apparatus according to claim 8, further comprising a first pressure sensor coupled to an inlet of the microchannel.

10. A microfluidic apparatus according to claim 9, further comprising a second pressure sensor coupled to an outlet of the microchannel.

11. A microfluidic apparatus according to claim 1, further comprising:
a sensor arranged to sense fluid in the non-tapered narrow section of the least one microchannel segment; and
a computer coupled to the sensor for identifying a parameter of the fluid in the microchannel based on information received from the sensor.

12. A microfluidic apparatus according to claim 11, wherein the sensor comprises at least one of a capacitive/impedance sensor, an acoustic sensor, and a piezoelectric sensor.

13. A method of a measuring a parameter of a fluid containing hydrocarbons, comprising:
introducing the fluid into a microchannel including at least one vertically-oriented segment, each segment having:
a wide section having a first opening,
a non-tapered narrow section having a second opening, and
a tapered section between the wide and non-tapered narrow sections, the tapered section tapering down from the wide section to the non-tapered narrow section, wherein the first opening is wider than the second opening, and the wide section is larger in volume relative to the non-tapered narrow section, wherein the at least one segment comprises at least two segments arranged in series or wherein the at least one segment comprises at least two segments arranged in parallel with the wide sections of all of the segments coupled by a first fluid line, and the non-tapered narrow sections of all of the segments coupled by a second fluid line;
modifying at least one of a pressure and a temperature of the fluid in the microchannel;
monitoring the microchannel to identify a change of state of fluid in the microchannel; and
measuring a parameter of the fluid based on the change of state.

14. A method according to claim 13, wherein the parameter is a dew point of the fluid.

15. A method according to claim 13, wherein the parameter is a liquid drop-out as a function of pressure.

16. A method according to claim 13, wherein the monitoring comprises:
illuminating at least the non-tapered narrow section of the at least one microchannel segment;
sensing light which is at least one of reflected from and transmitted through the non-tapered narrow section of the microchannel segment; and
identifying a parameter of the fluid in the microchannel based on information received from the light sensor.

17. A method according to claim 16, wherein the parameter is a liquid drop-out as a function of pressure, and the method further comprises plotting the liquid drop-out as a function of pressure.

18. A method according to claim 16, wherein the parameter is a dew point of the fluid, and the modifying comprises reducing the pressure on the fluid in the microchannel at least until liquid is identified.

19. A method according to claim 18, further comprising increasing the pressure in the microchannel to find a pressure at which the liquid disappears.

* * * * *